United States Patent
Kaneko et al.

(10) Patent No.: US 9,121,846 B2
(45) Date of Patent: Sep. 1, 2015

(54) DAIKENCHUTO BIOASSAY METHOD AND QUALITY MANAGEMENT METHOD USING SAME

(75) Inventors: Atsushi Kaneko, Ibaraki (JP); Nagisa Ohno, Ibaraki (JP)

(73) Assignee: TSUMURA & Co., Tokyo (JP)

( * ) Notice: Subject to any disclaimer, the term of this patent is extended or adjusted under 35 U.S.C. 154(b) by 0 days.

(21) Appl. No.: 13/991,174

(22) PCT Filed: Nov. 28, 2011

(86) PCT No.: PCT/JP2011/077360
§ 371 (c)(1),
(2), (4) Date: Jun. 3, 2013

(87) PCT Pub. No.: WO2012/073881
PCT Pub. Date: Jun. 7, 2012

(65) Prior Publication Data
US 2013/0260401 A1 Oct. 3, 2013

(30) Foreign Application Priority Data
Dec. 3, 2010 (JP) ................................. 2010-270643

(51) Int. Cl.
*G01N 33/50* (2006.01)
*G01N 33/94* (2006.01)

(52) U.S. Cl.
CPC .......... *G01N 33/5008* (2013.01); *G01N 33/507* (2013.01); *G01N 33/5064* (2013.01); *G01N 33/94* (2013.01); *G01N 33/942* (2013.01); *G01N 2333/415* (2013.01); *G01N 2333/70571* (2013.01)

(58) Field of Classification Search
None
See application file for complete search history.

(56) References Cited

U.S. PATENT DOCUMENTS 7,022,489 B2 * 4/2006 Bard et al. ...................... 435/7.2
2010/0129345 A1 * 5/2010 Nozawa et al. ............ 424/130.1

FOREIGN PATENT DOCUMENTS

WO WO 9739355 A1 * 10/1997 ............. G01N 33/50
WO WO 9921007 A1 * 4/1999 ............. G01N 33/50
WO WO 2008141392 A1 * 11/2008 ............. G01N 33/04

OTHER PUBLICATIONS

Satoh et al., Dai-kenchu-to Enhances Accelerated Small Intestinal Movement, Bio. Pharm. Bull. 24 (10), 1122-1126 (2001).*
Iwabu et al., Profiling of the Compounds Absorbed in Human Plasma and Urine after Oral Administration of Traditional Japanese (Kampo) Medicine, Daikenchuto, Drug Metabolism and Disposition, 38, 2040-2048, 2010.*
Nagano, T. et al., "Effects of Dai-Kenchu-to on Levels of 5-Hydroxytryptamine (Serotonin) and Vasoactive Intestinal Peptides in Human Plasma", Biol. Pharm. Bull., vol. 23, No. 3, pp. 352-353, (2000).
Nagano, T. et al., "Effect of Dai-Kenchu-to on Levels of Gastrointestinal Hormones", TDM Kenkyu, vol. 17, No. 2, pp. 151-152, (2000).
Sato, Y. et al., "Effects of Pirenzepine on Dai-kenchu-to-Induced Elevation of the Plasma Neuropeptide Levels in Humans", Biol. Pharm. Bull., vol. 29, No. 1, pp. 166-171, (2006).
Kan, H. et al., "Herbal Medicine Therapies for Digestive Disease: A Special Focus on Dai-kenchu-to", Journal of Medical Associattion of Nippon Medical School, vol. 6, No. 3, pp. 127-129, (Jun. 2010).
Kase, Y. et al., "Literature for the Research of Kampo Medicine", Pharmacology Research Dept., R&D Division, Tsumura & Co., vol. 120, No. 10, pp. 544-548, (Oct. 2006).
Kano, T. et al., "A Possible Mechanism by Which Daikenchuto (TU-100) Improves Intestinal Motility by Inducing Serotonin Release From Enterochromaffin Cells by the Transient Receptor Potential Al Channel", Gasteroenterology, vol. 140, No. 5, Suppl.1, p. S523, Su1971, (May 2011).
International Search Report Issued Dec. 20, 2011 in PCT/JP11/077360 Filed Nov. 28, 2011.
Search Report dated Dec. 10, 2014 issued in corresponding European patent application No. 11844371.2.
Mochiki et al.—"The Effect of Traditional Japanese Medicine (Kampo) on Gastrointestinal Function", Surgery Today (2010), 40 pp. 1105-1111.
Doihara et al.-—"QGP-1 cells release 5-HT via TRPA1 activation; a model of human enterochromaffin cells", Mol. Cell Biochem (2009) 331, pp. 239-245.
Wood et al.—"The Effects of Daikenchuto (DKT) on Propulsive Motility in the Colon", Journal of Surgical Research (2010) 164, pp. 84-90.
Tokita et al.—The Pharmacological Effects of *Daikenchuto*, a Traditional Herbal Medicine, on Delayed Gastrointestinal Transit in Rat Postoperative Ileus, Journal of Pharmacological Sciences, (2007) 104, pp. 303-310.

* cited by examiner

*Primary Examiner* — Galina Yakovleva
*Assistant Examiner* — Andrea S Grossman
(74) *Attorney, Agent, or Firm* — Oblon, McClelland, Maier & Neustadt, L.L.P.

(57) ABSTRACT

The invention intends to provide a bioassay method using a simple in-vitro test for Daikinchuto, and further to provide a more highly accurate method for quality control of Daikenchuto using the same. These methods are a bioassay method for the pharmacological activity of Daikenchuto, characterized in that a test sample containing Daikenchuto is added to cultured serotonin-producing cells, and the serotonin content in the culture supernatant is subsequently measured; and a quality control method for Daikenchuto preparations in which the pharmacological activity of a test preparation and a reference preparation for which the pharmacological effect as Daikenchuto has been clinically confirmed are evaluated under the same conditions, and the equivalence of the reference preparation and testing preparation is evaluated.

17 Claims, 2 Drawing Sheets

(a)

RETENTION TIME (MIN)

(b)

RETENTION TIME (MIN)

DAIKENCHUTO BIOASSAY METHOD AND QUALITY MANAGEMENT METHOD USING SAME

TECHNICAL FIELD

The present invention relates to a bioassay method for Daikenchuto, more specifically to a bioassay method capable of quantitatively determining the pharmacological activity value (serotonin release activity) of Daikenchuto, a type of kampo preparation, by the use of cultured serotonin-producing cells, and to a quality control method for Daikenchuto using the bioassay method.

BACKGROUND ART

A kampo preparation is a pharmaceutical prepared by blending crude drugs, in which all the active ingredients are not always specifically identified. Furthermore, a single active ingredient alone does not always exhibit its effect, and some active ingredients may compositely act with each other. For assuring its quality, it is said that an assay method capable of totally evaluating the whole kampo preparation is necessary. Indeed, the U.S. Food and Drug Administration Guidance for Industry on Botanical Drug Products calls for a quality control using a bioassay and the like for products such as kampo preparations.

Assay methods include a method that measures and comprehensively evaluates all the components thought to have efficacy, and a bioassay method of evaluating the physiological activity by the use of a biological material. The former method is problematic in terms of measurement costs and establishing a measurement method. Bioassay methods include an in-vivo test and an in-vitro test, and the in-vivo test system has many limitations regarding the test facilities, test animals, the processing capability, and the like, and there are difficulties in applying the in-vivo test to the quality evaluation of kampo preparations.

On the other hand, the in-vitro test system does not require any special facilities and gives stable test results in a short period of time. For this reason, an in-vitro bioassay method is desirable. However, for a kampo preparation that comprises a combination of crude drugs each having plural active ingredients, a suitable bioassay system has not yet been reported, and such a bioassay system is desired.

To date, a method that directly measures the contraction of enteric smooth muscle following Daikenchuto administration (the Magnus method) has been established as a bioassay method for the quality control of the pharmacological effect of the kampo preparation Daikenchuto (Non-Patent Document 1).

However, because the Magnus method uses the intestinal tract isolated from a rat, it has poor utility as a bioassay method conducted as a routine test for quality evaluation, and is insufficient in terms of qualities such as sensitivity and reproducibility.

PRIOR ART DOCUMENTS

Patent Documents

Non-Patent Document 1: The Medical Association of Nippon Medical School, Vol. 6 (3), pp. 127-129 (2010), Hayato Kan, and Eiji Uchida

DISCLOSURE OF THE INVENTION

Problems that the Invention is to Solve

It is accordingly an object of the present invention to provide a bioassay method that uses a simple in-vitro test for Daikenchuto, and a highly accurate method for quality control of Daikenchuto using the bioassay method.

Means for Solving the Problems

The present inventors focused on reports of the intestinal motility enhancing effect and the intestinal blood flow increasing effect of Daikenchuto, and involvement of serotonin in these effects (Non-Patent Document 1), and conducted intensive studies of relationships between Daikenchuto and serotonin. It was found as a result that Daikenchuto has a serotonin release promoting effect for serotonin-producing cells, and that the pharmacological activity value of Daikenchuto can be determined through measurements of the released serotonin levels. It was also found that an appropriate quality control of Daikenchuto is possible with the use of such a bioassay system. The present invention has been completed on the basis of these findings.

Specifically, the present invention provides a bioassay method for Daikenchuto pharmacological activity. The method includes adding a Daikenchuto-containing test sample to cultured serotonin-producing cells, and measuring the serotonin content in a culture supernatant.

The present invention also provides a quality control method for Daikenchuto preparations. The method includes evaluating the pharmacological activity of a reference preparation whose pharmacological effect as Daikenchuto is clinically confirmed and the pharmacological activity of a test preparation under equal conditions by the use of the bioassay method, and evaluating the reference preparation and the test preparation for equivalence.

Effects of the Invention

The bioassay method of the present invention enables the pharmacological activity value (serotonin release activity) of Daikenchuto to be determined in a simple in-vitro test without limitation on the test facilities, test animals, the processing capability, and the like, and can realize a highly accurate quality control of Daikenchuto by conducting the test in an appropriate concentration range for quality evaluation.

MODE FOR CARRYING OUT THE INVENTION

Figure 1:
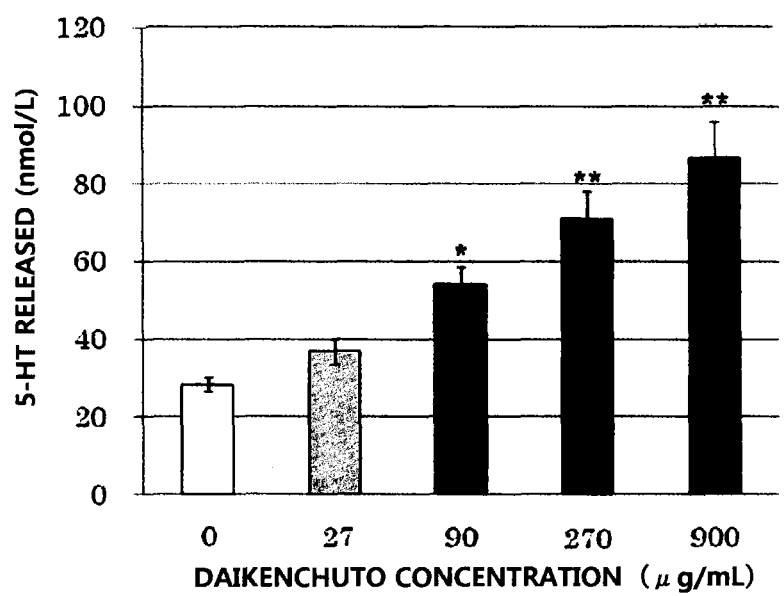
FIG. 1 is a diagram representing the relationship between Daikenchuto concentration and the amount of released serotonin (5-HT).

Typical Daikenchuto is a mixture prepared from a powder of an extract from a crude drug mixture of the composition presented in Table 1 (often called "Koi-free Daikenchuto") and Koi (maltose) added in a powder form in about eight times the amount of the extract.

TABLE 1

| Name | Proportion |
| --- | --- |
| JP Processed Ginger | 5.0 g |
| JP Ginseng | 3.0 g |
| JP Zanthoxylum Fruit | 2.0 g |

The Daikenchuto to be evaluated in the bioassay method of the present invention encompasses Daikenchuto preparations prepared as granules or some other form from Daikenchuto by adding a component approved as an additive for medical products. Examples of such Daikenchuto preparations include commercially available medical products such as the Tsumura Daikenchuto extract granule (medical use).

Examples of the component approved as an additive for medical products include excipients (such as starch, lactose, sucrose, mannitol, carboxymethyl cellulose, corn starch, and inorganic salts), disintegrants, surfactants, lubricants, fluidity promoting agents, corrigents, coloring agents, and fragrances.

In the bioassay method for Daikenchuto of the present invention, a Daikenchuto-containing test sample is added to cultured serotonin-producing cells, and the pharmacological activity value of Daikenchuto is determined by measuring the amount of released serotonin in the cultured serotonin-producing cells after addition of the test sample.

Examples of the serotonin-producing cells for use in the present invention include enterochromaffin cells. The enterochromaffin cells are endocrine cells, capable of producing and secreting serotonin present in an organism in large quantities. The enterochromaffin cells in the intestinal tract are preferably used due to the fact that 90% of the serotonin present in an organism is located in the enterochromaffin cells of the intestinal tract.

Enterochromaffin-like cell lines capable of producing certain stable serotonin also may be used as the serotonin-producing cells. Examples of such enterochromaffin-like cell lines include rat pancreatic cancer-derived RIN-14B cells, human pancreatic cancer-derived QGP-1 cells, and human small intestine carcinoid-derived KRJ-I cells. Of these, the RIN-14B cells are particularly preferred for the reason that they are superior in proliferation.

In the bioassay method for Daikenchuto of the present invention, the serotonin-producing cells are first cultured in a suitable growth medium such as an RPMI 1640 medium supplemented with an antibiotic and a serum, for example, for 1 day to 3 days at 37° C. After replacement with a phosphate buffer or the like, a predetermined amount of a test sample is added, and the cells are cultured for 20 minutes to 3 hours at the same temperature. The amount of the serotonin released into the medium is then measured.

Typically, the Daikenchuto-containing test sample is added to the medium after being dissolved or suspended in a solvent such as dimethylsulfoxide (DMSO).

The method used to measure the amount of released serotonin is not particularly limited and a known method may be used, as long as it can measure the released serotonin level. Preferred examples include enzyme immunoassay (EIA) and HPLC.

In the EIA used in the present invention, the activity of the enzyme attached to an antigen or an antibody that elicits a specific antigen-antibody reaction is measured to determine the binding of the antigen-antibody reaction. Specifically, the method may be performed by using commercially available kits, such as the EIA serotonin kit (Beckman Coulter).

For the measurement of the amount of released serotonin by high-performance liquid chromatography (HPLC), measurement conditions such as the amount of the charged sample, the type of the analysis column, the diameter and length of the analysis column, the temperature of the analysis column, the composition of the mobile phase, and the flow rate of the mobile phase may be appropriately selected so as to be optimal for serotonin isolation. Preferably, conditions are selected to avoid an overlap in the retention times of serotonin and other detected products. A common column such as an ODS-charged column may be used as the analysis column, and a common electrochemical detector (ECD) may be used as the detector.

In the bioassay method of the present invention, it is preferable to quantify the pharmacological activity value (serotonin release activity) of Daikenchuto in a test sample by simultaneously taking measurements at more than one, preferably three or more measurement points, in a concentration range (0 to 900 µg/mL) in which the reaction takes place in a concentration-dependent fashion, more preferably in a concentration range (90 to 900 µg/mL) in which the reaction is statistically significant, as can be seen in the results of Example 1. However, so far as the condition is almost the same, a calibration curve previously prepared from samples each containing Daikenchuto in the foregoing concentration ranges may be used for the measurement.

For the quality evaluation of Daikenchuto as a product using the bioassay method of the present invention, the pharmacological activity value (serotonin release activity) is measured firstly for multiple lots of Daikenchuto whose pharmacological effect has been clinically confirmed, and a standard range is set from the measured values. Next, the pharmacological activity value (serotonin release activity) of a quality-test sample of Daikenchuto to be evaluated is measured by using the same method. The pharmacological activity value of the sample is then evaluated for equivalence by using the preset standard range as a reference. Thus products found to be equivalent can be determined to be acceptable in the quality control.

EXAMPLES

The present invention is described in more detail with reference to the following Examples. However, the invention should not be whatsoever restricted at all by these Examples.

Example 1

Daikenchuto Bioassay Test (1) Preparation of Test Sample

The crude drug mixture of the proportions presented in Table 1 was extracted by heating at 100° C. for 1 hour with purified water used in 10 times the amount of the mixture weight, and the extract was processed into a powder to obtain a Koi-free Daikenchuto extract powder. The Koi-free Daikenchuto extract powder was used to prepare a 100 mg/mL DMSO suspension, and the suspension was mixed with an 88.8 mg/mL maltose aqueous solution at a 1:9 ratio to prepare a 90 mg/mL Daikenchuto solution. The solution was diluted with 0.1% BSA-Hanks buffer* to make the concentration 9 mg/mL and subjected to 15-min sonication to prepare a Daikenchuto test sample.

Separately, a DMSO solution of 100 mmol/L AITC was prepared as a positive control sample by adding allyl isothiocyanate (AITC; Wako Pure Chemical Industries, Ltd.) to DMSO.

*0.1% BSA-Hanks Buffer

Bovine serum albumin (1 g), glucose (1 g), sodium chloride (8 g), potassium chloride (400 mg), disodium phosphate (anhydrous; 47.9 mg), potassium dihydrogen phosphate (anhydrous; 60 mg), magnesium chloride (anhydrous; 46.8 mg), magnesium sulfate (anhydrous; 48.8 mg), and calcium chloride (anhydrous; 140 mg) were dissolved in 1 liter of distilled water, and the pH was adjusted to 7.2 to 7.4.

(2) Serotonin-Producing Cell (RIN-14B Cell) Culture

Rat pancreatic cancer cell line RIN-14B (DS Pharma Biomedical Co., Ltd.) was subcultured in an RPMI 1640 medium (10 mmol/L HEPES, 1.5 g/L $NaHCO_3$, 100 U/mL penicillin G, and 100 µg/mL streptomycin) supplemented with 10% fetal bovine serum (FBS) to prepare serotonin-producing cells. The cells were collected with a trypsin-EDTA solution.

(3) Serotonin (5-HT) Release Test

The serotonin-producing cells obtained in (2) were dispensed into a 96-well flat-bottom plate ($3\times10^4$ cells/100 µL/well). After 72-hour preculture, the culture supernatant was replaced with the 0.1% BSA-Hanks buffer containing each test sample obtained in (1). The cells were further cultured for 1 hour in a 5% carbon dioxide gas incubator.

The test sample was serially diluted with 1% DMSO-containing 0.1% BSA-Hanks buffer, and was added to make the final concentrations 27, 90, 270, and 900 µg/mL in the culture system. The final concentration of the DMSO in the culture system was 0.1%. In the positive control group, the positive control sample obtained in (1) was added instead of the test sample to make the final concentration 100 µmol/L in the culture system. The final concentration of the DMSO in the culture system was 0.1%.

Finally, the culture supernatant was centrifuged (320 g) for 5 min at 4° C., and the supernatant was used as a 5-HT concentration measurement sample (hereinafter, "measurement sample").

(4) Serotonin (5-HT) Measurement by EIA

The EIA measurement of the released 5-HT was performed with an EIA serotonin kit (Beckman Coulter) according to the manufacturer's protocol.

Specifically, the measurement sample obtained in (3) was placed in a tube charged with an acylation reagent, and, after adding an acylation buffer (50 the mixture was stirred with a vortex mixer until the reagent dissolved. The reaction was allowed to proceed at room temperature under shaded conditions for 30 minutes to obtain an acylated reaction liquid. The same process was performed for the system containing no measurement sample, and the product was used as a control.

Each acylated reaction liquid (20 µL) was then transferred into appropriate wells in a 96-well plate coated with anti-5-HT antibodies. After adding acetylcholine esterase (ACE)-5-HT conjugate (200 the sample was competitively incubated at room temperature under shaded conditions for 3 hours while being shaken with a plate mixer.

The plate was washed three times with a washing buffer attached to the kit (300 µL/well) to remove the free components. The sample was left unattended for 15 to 20 minutes after adding an ACE substrate (200 µL/well). After confirming the development of color, the reaction was stopped by adding a reaction stopper (50 and the absorbance at 405 nm was measured. The results are presented in FIG. 1.

As shown by the results in FIG. 1, the amount of 5-HT in the supernatant were evidently higher in the measurement samples that contained 27, 90, 270, and 900 µg/mL Daikenchuto than in the Daikenchuto-free control. Further, the release was concentration dependent, sufficient to enable creation of a calibration curve. The positive control measurement sample with AITC also had an evidently higher 5-HT concentration than the control, demonstrating that the Daikenchuto had acted on the serotonin-producing cells to release 5-HT.

(5) Serotonin (5-HT) Measurement by HPLC

The cultured sample solution of 900 µg/mL Daikenchuto from the measurement samples obtained in (3), and the control cultured sample solution were measured by HPLC, and the 5-HT contained in each sample was detected. The results are presented in FIG. 2, (a) and (b) (5-HT retention time: 16.27 min in (a), and 16.11 min in (b)).

The HPLC analysis of 5-HT was performed under the following conditions. The 5-HT standard solution was prepared from a 0.1 mol/L acetic acid aqueous solution by adding EDTA in a final concentration of 100 mg/L.

HPLC Analysis Conditions
Trace biosample analysis system: HTEC-500 (EICOM)
Data processor: EPC-300 (EICOM)
Data analysis software: PowerChrom version 2.5.7 (eDAQ)
Analysis column: EICOMPAK CA-50DS, 2.1 mm φ×150 mm
Precolumn: EICOM PREPAKSET-CA, 3.0 mm φ×4 mm
Mobile phase: 80% 0.1 M phosphate buffer ($Na^+$) pH 6, 20% methanol, 500 mg/L sodium 1-octylsulfonate (SDS), 50 mg/L $EDTA.2Na^+$
Flow rate: 230 µL/min
Analysis temperature: 25° C.
Preset applied voltage: +450 mV (+400 to +450 mV) vs. Ag/AgCl
Working electrode: graphite electrode WE-3G
Gasket: GS-25
Analysis column: 80%

Figure 2:
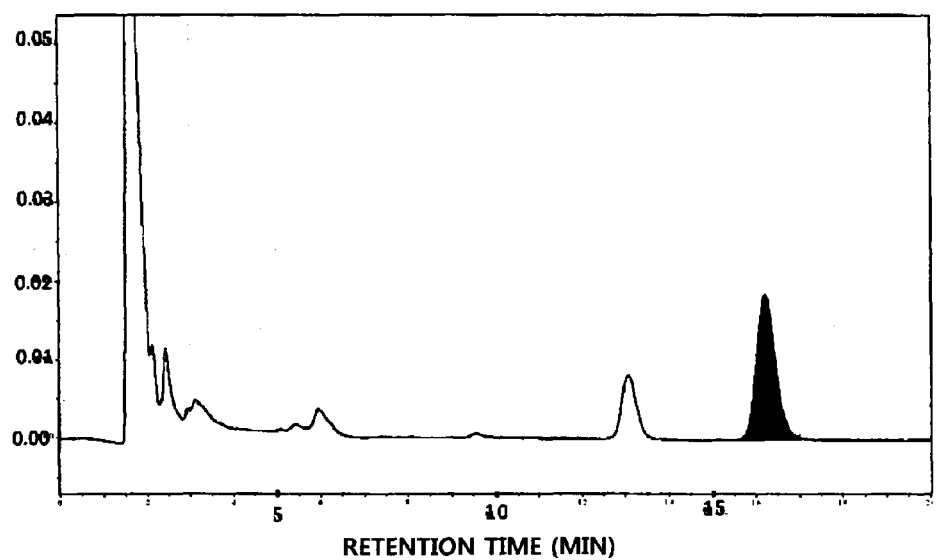
FIG. 2 is a diagram representing the results of the HPLC measurement of serotonin in a cultured sample solution, in which (a) represents released serotonin (5-HT) without addition of Daikenchuto, and (b) represents released serotonin (5-HT) with addition of 900 μg/ml Daikenchuto.
Figure 2:
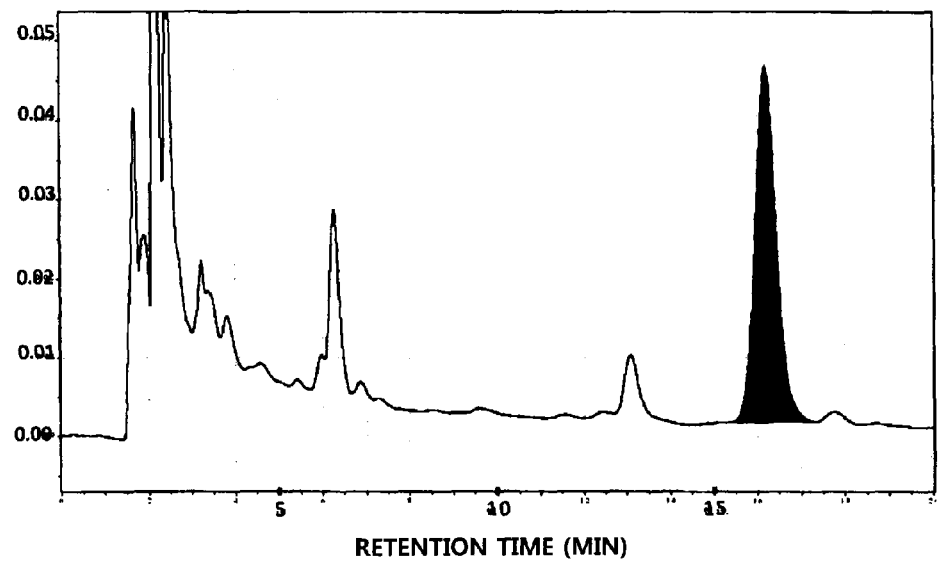

It was found from the results in FIG. 2 that the measurement of serotonin release activity was also possible by HPLC measurement.

INDUSTRIAL APPLICABILITY

The present invention enables testing for the quality evaluation of Daikenchuto without limitations on the test facilities, test animals, the processing capability, and the like, and can realize a highly accurate quality evaluation of Daikenchuto through testing conducted in an appropriate concentration range.

The present invention is thus superior to the conventional bioassay methods for Daikenchuto in terms of economy, and enables a quality evaluation to be performed more conveniently. The present invention is therefore highly advantageous in the quality control of kampo preparations.

The invention claimed is:

1. A method for determining pharmacological activity of a Daikenchuto sample comprising:
   contacting in vitro a cultured serotonin-producing cell with the sample of Daikenchuto at a concentration ranging from >0 to 900 µg/ml for a time and under conditions sufficient for the cell to secrete serotonin (5-HT) into the cell culture medium;
   quantifying the amount of serotonin released into the cell culture medium compared to an amount released from an otherwise identical negative control that was not contacted with Daikenchuto; wherein the amount of serotonin (5-HT) released linearly correlates with pharmacological activity of the Daikenchuto sample.

2. The method of claim 1, wherein said concentration ranges from 27 to 900 µg/ml.

3. The method of claim 1, wherein said concentration ranges from 90 to 900 µg/ml.

4. The method of claim 1, wherein the pharmacological activity comprises an intestinal motility enhancing effect or an intestinal blood flow increasing effect.

5. The method of claim 1, wherein the amount of serotonin (5-HT) released ranges from about 40 to about 80 mmol/L.

6. The method of claim 1, wherein the amount of serotonin (5-HT) released ranges from about 60 to about 80 mmol/L.

7. The method of claim 1, wherein the sample of Daikenchuto is dissolved or suspended in an aqueous solution or buffer and sonicated prior to contacting it with said cells.

8. The method of claim 1, wherein the sample of Daikenchuto is dissolved or suspended in a DMSO (dimethylsulfoxide) solution prior to contacting it with said cells.

9. The method of claim 1, wherein the sample of Daikenchuto is diluted to different concentrations within the range of >0 to 900 µg/ml and the different concentrations are contacted with separate samples of the cells.

10. The method of claim 1, wherein said cells are endocrine cells that produce serotonin (5-HT).

11. The method of claim 1, wherein said cells are enterochromaffin cells that produce serotonin (5-HT).

12. The method of claim 1, wherein said cells are RIN-14B cells that produce serotonin (5-HT).

13. The method of claim 1, wherein said cells are QGP-1 cells, KRJ-I cells or other enterochromaffin-like cells that produce serotonin (5-HT).

14. The method of claim 1, wherein the amount of serotonin released is quantified by enzyme immunoassay (EIA).

15. The method of claim 1, wherein the amount of serotonin (5-HT) released is quantified by high-performance liquid chromatography (HPLC).

16. The method of claim 1 that quantifies the pharmacological activity of a Daikenchuto preparation.

17. The method of claim 1, further comprising determining the relative pharmacological activity of two or more Daikenchuto samples.

* * * * *